United States Patent [19]

Celmer et al.

[11] 4,032,631

[45] June 28, 1977

[54] MIXTURE OF ANTIBIOTICS PRODUCED BY NEW SPECIES OF MICROMONOSPORA

[75] Inventors: Walter D. Celmer, New London; Walter P. Cullen, East Lyme; Charles E. Moppett, Mystic; John R. Oscarson, Groton; John B. Routien, Lyme, all of Conn.; Riichiro Shibakawa; Junsuke Tone, both of Aichi, Japan

[73] Assignee: Pfizer Inc., New York, N.Y.

[22] Filed: Dec. 19, 1975

[21] Appl. No.: 642,296

[52] U.S. Cl. .............................. 424/120; 424/121; 424/115; 195/80 R
[51] Int. Cl.² ...................................... A61K 35/74

[58] Field of Search ................. 424/120, 121, 115; 195/80 R

[56] References Cited
UNITED STATES PATENTS 3,335,057  8/1967  Johnson et al. .................. 424/119

Primary Examiner—Jerome D. Goldberg
Attorney, Agent, or Firm—Connolly and Hutz

[57] ABSTRACT

A new species of Micromonospora, designated *Micromonospora saitamica* sp. nov. Routien, when subjected to submerged aerobic fermentation, produces at least four antibiotics. One of these is previously reported rubradirin produced by *Streptomyces achromogenes* var. *rubradiris* NRRL 3061.

4 Claims, 4 Drawing Figures

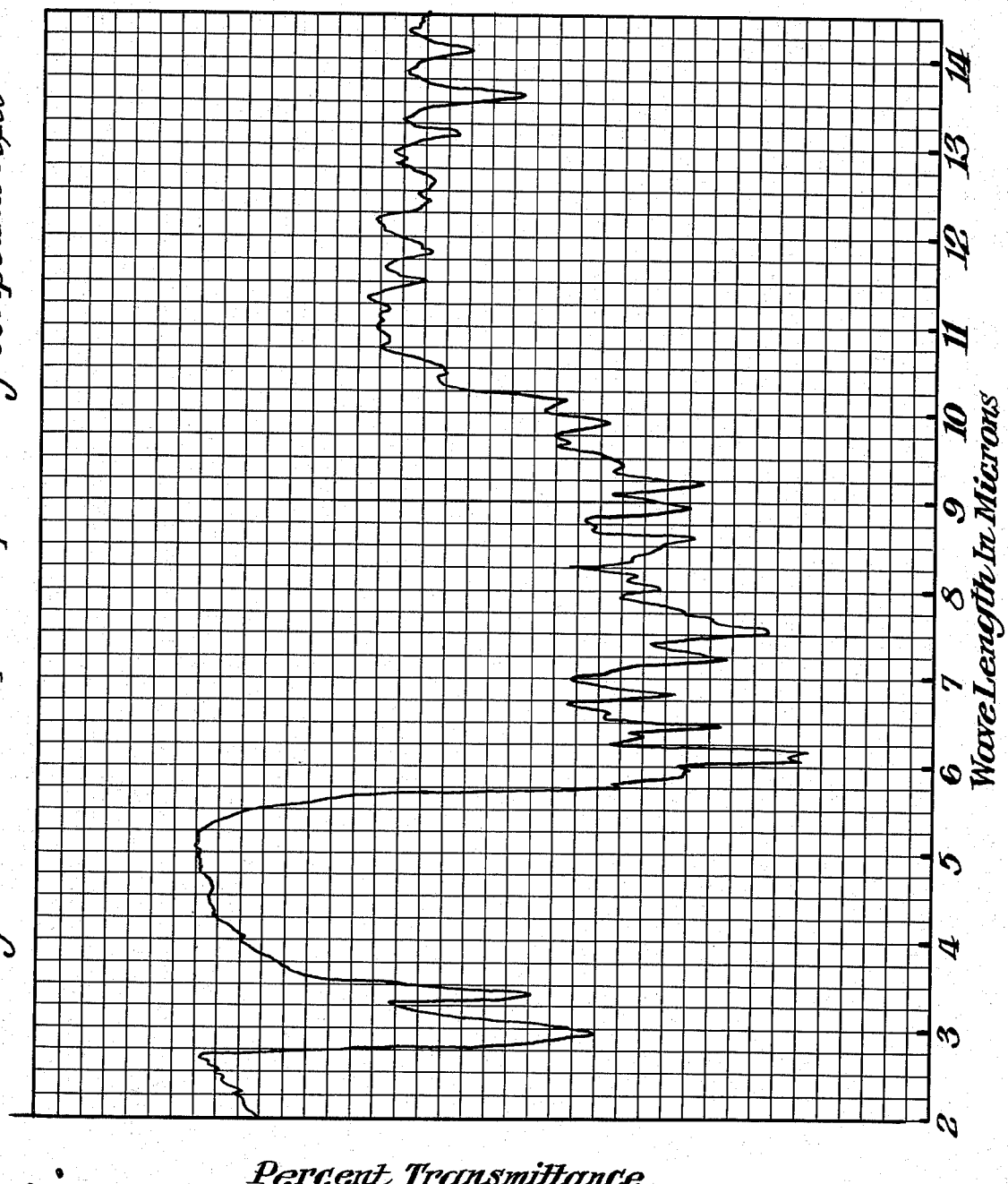

MIXTURE OF ANTIBIOTICS PRODUCED BY NEW SPECIES OF MICROMONOSPORA

BACKGROUND OF THE INVENTION

The search for new antibiotics produced by soil microorganisms has encompassed the screening of various genera of bacteria, higher bacteria and fungi including many species within each genus and many strains within each species.

Microorganisms that are receiving increasing attention include the genus Micromonospora, a genus closely resembling Streptomyces but differing in the lack of aerial mycelium and with very narrow hyphae on which minute spores are borne singly.

SUMMARY OF THE INVENTION

This invention is concerned with Compounds 42,405, 42,752, 43,038 and 43,139, antibiotics produced under submerged aerobic fermentation conditions by *Micromonospora saitamica* sp. nov. Routien ATCC 31178. Compounds 42,752, 43,038 and 43,139, whose characteristic infrared curves are reproduced in FIGS. 1 through 3, are new antibiotics while Compound 42,405 is identical with previously reported rubradirin produced by *Streptomyces achromogenes var. rubradiris* NRRL 3061 (see U.S. Pat. No. 3,335,057). Methods for the recovery and purification of these antibiotics are described and some of their antimicrobial properties are outlined.

DETAILED DESCRIPTION OF THE INVENTION

Figure 1:
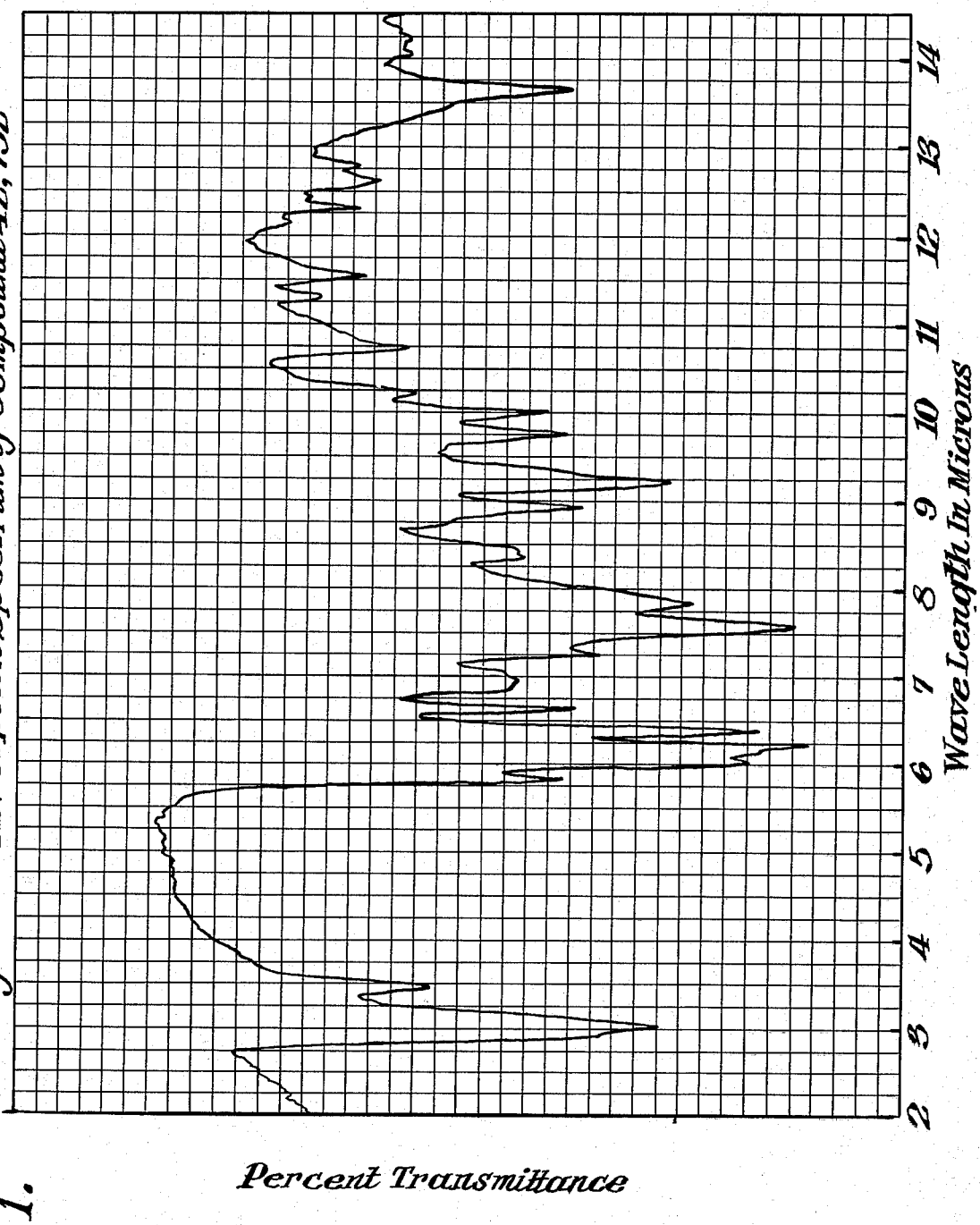

The microorganism useful for the preparation of the antibiotics of this invention was isolated from a soil sample from Japan. This culture (Pfizer F.D. 24430), designated *Micromonospora saitamica* sp. nov. Routien, has been deposited in The American Type Culture Collection, Rockville, Md. as the type culture under their accession number ATCC 31178. The permanency of the deposit and ready accessibility thereto by the public are afforded in the event the patent is granted. Access to the culture is available during pendency of the application under Rule 14 and 35 USC 112. All restrictions on the availability to the public of the culture deposited will be irrevocably removed upon granting of the patent.

The culture was incubated at 28° C. unless otherwise stated and records of results were made after suitable incubation time. The descriptive code of colors of the mycelium was that of the *Color Harmony Manual*, 4th edition, The Container Corporation of America, 1958.

The media or tests and appropriate references are as follows:
1. Potato Carrot Agar - M. P. Lechevalier, Jr. Lab. and Clinical Med. 71: 934–944, 1968 but made with 30 g potatoes and 2.5 g carrots and 20 g agar.
2. Tap Water Agar - 2% agar and tap water.
3. Glucose - Asparagine Agar - Waksman, S. A., The Actinomycetes, Vol. 2, medium no. 2 on p. 328, 1961.
4. Glucose Yeast Agar - Waksman, S. A., medium no. 29, p. 331, 1961.
5. Czapek - Sucrose Agar - Waksman, S. A., medium no. 1, p. 328, 1961.
6. Emerson's Agar - Waksman S. A., medium no. 28, p. 331, 1961.
7. Gelatin - R. E. Gordon and J. M. Mihm, Jr. Bact. 73: 15–27, 1957.
8. Starch Agar - R. E. Gordon and J. M. Mihm, Jr. Bact. 73, 15–27, 1957.
9. Tyrosine Agar - R. E. Gordon and M. M. Smith, Jr. Bact. 69: 147–150, 1955.
10. Skim Milk (Difco)
11. Peptone Iron Agar (Difco) with Lead Acetate Strips.
12. Potato Slices with and without $CaCO_3$ - G. M. Luedemann and B. C. Brodsky, Antimicrobial Agents and Chemotherapy 1964, pg. 47–52.
13. Sucrose Invertase - M. Levine and H. W. Schoenlein, A Compilation of Culture Media, medium no. 622, 1930.
14. Cellulose Digestion -
   a. H. L. Jensen, Proc. Linnean Soc. N. S. Wales 55: 231–248, 1930.
   b. M. Levine and H. W. Schoenlein, medium no. 2511, 1930.
15. Temperature Range - ATCC Medium no. 172 in American Type Culture Catalog tenth edition, p. 235, 1972.
16. Tryptone Yeast Extract Broth - T. G. Pridham and D. Gottlieb, Jr. Bact. 56: 107–114, 1948.
17. Dextrose Nitrate Broth - Waksman, S. A., The Actinomycetes, medium no. 1 with 3 g dextrose in place of sucrose and agar omitted, p. 193, 1950.
18. Organic Nitrate Broth - R. E. Gordon and J. M. Mihm, Jr. Bact. 73, 15–27, 1957.
19. NaCl Tolerance - G. M. Luedemann, Advances in Applied Microbiology 11: p. 123, 1969.
20. Nitrogen Utilization - M. J. Weinstein et al., Antimicrobial Agents and Chemotherapy 1967, p. 437, 1968.
21. Carbohydrate Utilization - Luedemann and Brodsky, 1965.
22. Hyphal Study - Luedemann and Brodsky, 1965.

The description of the culture and test results are as follows:

Potato-Carrot Agar - Growth poor, thin, flat, gray with black sporulated areas, reverse colorless; no soluble pigment.

Glucose-Yeast Extract Agar - Growth good, thick, with raised black masses on a thin, flat streak near 4 ga in color; reverse near 4 ga with black areas showing through agar; slight brown soluble pigment.

Emerson's Agar - Growth good, consisting of raised heaps of tissue either cream-colored or grayish-black; reverse cream-colored to grayish-black in different areas.

Gelatin - Growth poor, thin, flat, colorless but with occasional black spots; reverse colorless; no soluble pigment.

Starch Agar - Growth very poor, thin, colorless; reverse colorless; no soluble pigment.

Potato Slice (No. $CaCO_3$) - Growth poor, consisting of small isolated spots ranging in color from cream-colored to gray or black; no soluble pigment.

Potato Slice (with $CaCO_3$) - Growth good, raised, roughened, from 4 ia to mostly black; no soluble pigment.

Glucose - Asparagine Agar - Growth very poor, colorless and thin except for small black masses of spores, reverse colorless with black areas; no soluble pigment.

Czapek - Sucrose Agar - Growth very poor, thin, flat, colorless except for blackish specks; reverse colorless with blackish specks; no soluble pigment.

Hyphal Study - In seven days of stationary incubation growth was moderate, narrow hyphae were typical of actinomycetes in their narrow width, branches were mostly at right angles, and there was no spore formation.

Spores - Spores on potato-carrot agar were borne on substrate mycelium in minute to large, dense masses that made black spots on the colony. Spores were round, 1.5 $\mu$m wide to oval, 1.5 × 1.0 $\mu$m. Scanning electron micrographs showed the surface to be warty.

Biochemical properties - No melanin in either tryptone yeast extract broth or on peptone iron agar slants; no $H_2S$ produced; starch weakly hydrolyzed (5 mm. zone in 7 days); gelatin moderately liquefied (9 mm. zone in 7 days); nitrate reduced to nitrite in both dextrose nitrate broth and organic nitrate broth; growth good on both cellulose media but no disintegration even in 28 days; skim milk partially coagulated by 14 days and peptonization begun; sucrose not inverted even after 28 days; growth in 1 to 3% NaCl but very little growth at 3% in the 7 days of incubation; good growth from 21° to 37° C but no growth at 45° C; nitrogen assimilation: no growth on $NaNO_3$ or glutamic acid, poor growth in spots on asparagine, thin colorless growth on NZ Amine A and good growth on yeast extract agar; carbon assimilation (ISP method): growth on glucose, arabinose, cellobiose, fructose, inositol, mannose, soluble starch, sucrose, trehalose and xylose; no growth on adonitol, dulcitol, galactose, glycerol, lactose, mannitol, melezitose, melibiose, raffinose, rhamnose, salicin, sorbitol and sorbose: doubtful results on ribose.

The properties of the culture were considered to be so different from those of known species of the genus that it was deemed to be a new and different species of the genus Micromonospora. It was named *Micromonospora saitamica* sp. nov. Routien after Saitama prefecture, Japan where the soil sample supplying the culture was collected.

Cultivation of the Micromonospora culture preferably takes place in nutrient media at a temperature of about 28°–36° C., and under aerobic, submerged conditions with agitation. Nutrient media which are useful for such purposes include a source of assimilable carbon such as sugars, starch, glycerol and molasses; a source of organic nitrogen such as fish meal, casein, enzymatic digest of casein, meat meal, wheat gluten, cottonseed meal, soybean meal and peanut meal. A source of growth substances such as distillers' solubles and/or yeast extract as well as salts such as sodium chloride, ammonium acetate, ammonium sulfate, potassium phosphate and trace minerals such as iron, magnesium, zinc, cobalt and manganese may also be utilized with advantageous results. If excessive foaming is encountered during fermentation, antifoam agents such as vegetable oils or silicones may be added to the fermentation medium. The pH of the fermentation tends to remain rather constant but if variations are encountered, a buffering agent such as calcium carbonate may also be added to the medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the microorganism and throughout its growth.

Inoculum for the preparation of the antibiotic may be obtained by employing growth from slants or Roux bottles of *M. saitamica* on such agar media as ATCC Medium 172 to which previous reference was made. The growth may be used to inoculate either shake flasks or inoculum tanks, or alternatively, the inoculum tanks may be seeded from the shake flasks. The growth of the microorganism usually reaches its maximum in about 2 or 3 days. However, variations in the equipment used, aeration, rate of stirring, etc. may affect the speed with which the maximum growth is reached. In general, the fermentation is conducted until substantial antimicrobial activity is imparted to the medium, a period of from about 24 hours to about 4 days being sufficient for most purposes.

The process of antibiotic production is conveniently followed during fermentation by biological assay of the broth employing a sensitive strain of *Staphylococcus aureus*. Standard plate assay technique is employed in which the zone of inhibition surrounding a filter paper disc saturated with the broth is used as a measure of antibiotic potency. After the fermentation broth has reached a desired level of antibiotic potency, the pH is usually about 7.5–8.5, the mycelium is removed by filtration or centrifugation.

Thin-layer chromatography employing silica gel is a useful tool for analyzing the antibiotics produced by *M. saitamica* in fermentation media and the composition of crude and purified materials extracted from fermentation broths. Silica gel buffered to pH 5.0 by spraying with pH 5.0 aqueous phosphate buffer followed by drying at about 110°–120° C. is employed with a developing system of chloroform:ethyl acetate (50:50% - v/v). The antibiotics appear as bright red spots on a white background. When chromatographed on silica gel buffered at pH 7.0, the Rf's of the components are reversed, and the antibiotics turn green on standing. The antibiotics are pigments and so may be observed by visual examination of the developed plates or by exposure of the developed plates to 254 nm light. Bioautographic detection of the antibiotic components may be accomplished by means of an overlay of a thin layer of agar seeded with a sensitive strain of *Staphylococcus aureus* or other sensitive organism on the developed silica gel chromatograms.

The antibiotics may be recovered from fermentation broth by a number of different procedures including solvent extraction and column chromatography or combinations thereof. Various organic solvents are useful in extracting the antibiotics from whole or clarified fermentation broth. Solvents such as n-butanol, methylisobutyl ketone, ethyl acetate and chlorinated hydrocarbons may be used at pH ranges from 2.0 to 8.0.

The preferred method of separation and recovery of the antibiotics of this invention is as follows: Whole fermentation broth is adjusted to pH 5.0 - v/v). 50% sulfuric acid and extracted with methylisobutyl ketone. The solvent extract is concentrated under vacuum and the antibiotics extracted into pH 10.0 aqueous phosphate buffer. The buffer extract is adjusted first to pH 8.0 and extracted with chloroform, then adjusted to pH 4.0 and extracted with fresh chloroform. The chloroform extracts are concentrated separately and the solids from each extract are precipitated by the addition of n-heptane. The materials are further purified by column chromatography with silica gel buffered at pH 5.0 developed with chloroform:ethyl acetate (80:20% -v/v).

The present invention includes within its scope the dilute forms and crude concentrates of the complex of antibiotics and the individual crude and purified antibiotic components. All of these products are useful in combatting microorganisms such as *Streptococcus pneumoniae*, *Streptococcus pyogenes* and *Staphylococcus aureus*. In addition they are useful as disinfectants against such microorganisms and as an aid in the purification of mixed cultures for medical, diagnostic and biological research purposes.

Table I illustrates the antibacterial spectra of the antibiotic components. These tests were run by preparing tubes of nutrient broth with gradually increasing concentrations of the pure antibiotic and then seeding the broths with the particular organism specified. The minimal inhibitory concentration indicated in Table I is the minimal concentration of the antibiotic (in micrograms/ml) at which the microorganism failed to grow. The tests were conducted under standardized conditions as described in Proc. Soc. Exp. Biol. & Med., 122, 1107 (1966).

Table I

| Organism | | Compound | | | |
| --- | --- | --- | --- | --- | --- |
| | | 43,139 | 43,038 | 42,752 | 42,405 |
| *Staphylococcus aureus* | 01A005 | 0.1 | 3.12 | 100 | 0.012 |
| | 01A052 | 0.1 | 3.12 | 100 | 0.012 |
| | 01A109 | 0.1 | 1.56 | 100 | 0.0016 |
| | 01A110 | 0.1 | 1.56 | 100 | 0.003 |
| | 01A111 | 0.1 | 1.56 | 100 | 0.003 |
| | 01A087 | 0.2 | 1.56 | 100 | 0.003 |
| | 01A400 | 0.39 | 1.56 | 50 | 0.003 |
| *Streptococcus faecalis* | 02A005 | >25 | >50 | >200 | 3.12 |
| *Streptococcus pyogenes* | 02C203 | 0.1 | 1.56 | 50 | 0.006 |
| *Mycobacterium smegmatis* | 05A001 | 25 | 6.25 | >200 | 0.10 |
| *Bacillus subtilis* | 06A001 | 12.5 | 12.5 | >200 | 0.025 |
| *Escherichia coli* | 51A266 | >25 | >50 | >200 | >200 |
| | 51A229 | >25 | >50 | >200 | >200 |
| | 51A125 | >25 | >50 | >200 | >200 |
| *Pseudomonas aeruginosa* | 52A104 | >25 | >50 | >200 | >200 |
| *Klebsiella pneumoniae* | 53A009 | >25 | >50 | >200 | >200 |
| | 53A031 | >25 | >50 | >200 | >200 |
| *Proteus mirabilis* | 57C064 | >25 | >50 | >200 | >200 |
| *Proteus morgani* | 57G001 | >25 | >50 | >200 | >200 |
| *Salmonella cholerae-suis* | 58B242 | >25 | >50 | >200 | >200 |
| *Salmonella typhi-murium* | 58D009 | >25 | >50 | >200 | >200 |
| | 58D013-C | >25 | >50 | >200 | >200 |
| *Pasteurella multocida* | 59A001 | >25 | >50 | 3.12 | >200 |
| *Serratia marcescens* | 63A017 | >25 | >50 | >200 | >200 |
| *Enterobacter cloaceae* | 55A004 | >25 | >50 | >200 | >200 |
| | 67A003 | >25 | >50 | >200 | >200 |
| *Neisseria sicca* | 66C000 | 0.39 | 1.56 | 0.003 | 0.003 |

The antibiotics of this invention can be administered via the oral or parenteral routes for the treatment in animals, including humans, of pneumococcal, streptococcal, staphylococcal, tubercular and other antibiotic-sensitive infections. In general, these antibiotics are most desirably administered in daily oral doses of 0.5–1 gram or parenteral injections of 100 to 500 mg., depending on the type and severity of the infection and weight of the subject being treated.

The compounds of this invention may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspensions and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerol and various combinations thereof.

For purposes of parenteral administration, solutions of these antibiotics in sesame or peanut oil or in aqueous propylene glycol may be employed.

The following examples are given to more fully illustrate the invention. It is to be understood that these examples are for illustrative purposes only and that the invention is not meant to be limited to the specific details of the examples.

EXAMPLE I

A sterile aqueous medium having the following composition was prepared:

| Ingredient | Grams/liter |
| --- | --- |
| Glucose | 10 |
| Starch | 20 |
| Yeast extract | 5 |
| Enzymatic digest of casein | 5 |
| Meat meal | 5 |
| K$_2$HPO$_4$ | 0.5 |
| CaCO$_3$ | 4 |
| CoCl$_2$ . 6H$_2$O | 0.002 |
| pH - 7.1–7.2 | |

Cells from a slant culture of *M. saitamica* ATCC 31178 were transferred to each of a number of 300 ml Erlenmeyer flasks containing 50 ml of the above medium and shaken at 28° C. on a rotary shaker for 3 to 4 days.

Fermentors containing 2 liters of the above described sterile medium were seeded with 5% v/v of the grown inoculum. The temperature was maintained at 28° to 36° C. and the broth was stirred at 1700 rpm and aerated at the rate of about one volume of air per volume of broth per minute. After about 48 to 72 hours, clarified broth or whole broth was twice extracted with ⅓ to ½ volume of chloroform or methylisobutyl ketone at pH 5.0. The solvent extract was concentrated under vacuum. The concentrate was shaken with 1/5 volume of aqueous pH 10.0 phosphate buffer, separated and the buffer extract adjusted first to pH 8.0 and extracted with 1/5 volume of chloroform, then 4.0 and extracted again with fresh chloroform. The individual chloroform extracts were concentrated to a thin syrup in vacuo and the antibiotics in each concentrate precipitated with n-heptane.

The bioactivity of the broth and subsequent recovery steps were followed by using a sensitive strain of *B. subtilis* PC 219 or *S. aureus* PC 209. The antibiotic components in the broth and crude concentrates were visualized by thin-layer chromatography employing pH 5.0 buffered silica gel plates with a developing system of chloroform:ethyl acetate (1:1 - v/v); the antibiotic Compound 42,405 is the least polar followed by Compound 43,139, Compound 43,038 and Compound 42,752 in that order. The antibiotics appeared as red spots against a white background. The plates were then overlayed with agar seeded with *S. aureus* or *B. subtilis* to confirm the bioactivity of the separated components.

EXAMPLE II

The fermentation process of Example I was repeated. About 5% of the grown inoculum was used to inoculate two 250 gallon fermentors each containing 100 gallons of the medium of Example I. After three to four days, a 10% v/v inoculum was transferred to two 1500 gallon tanks each containing 1000 gallons of the following sterile medium:

| Ingredient | Grams/liter |
| --- | --- |
| Glucose | 10 |
| Starch | 20 |
| Enzymatic digest of casein | 5 |
| Yeast extract | 5 |
| $CoCl_2 \cdot 6H_2O$ | 0.002 |
| $CaCO_3$ | 1.0 |
| pH - 7.2–7.3 | |

The fermentation was conducted at a temperature of 30° C. and an aeration rate of one volume of air per volume of broth per minute. After substantial antibiotic activity was obtained (approximately 48–72 hours), the whole fermentation broth was adjusted to pH 5.0 with 50% sulfuric acid and extracted with 400 gallons of methylisobutyl ketone by means of a Podbelniak extractor. The extract was washed twice with one-tenth volume of pH 10.0 aqueous phosphate buffer taking care to ensure that the pH of the aqueous layer remains at 10.0. The pH of the aqueous phase was dropped to 8.0 with 85% phosphoric acid and extracted twice with one-fifth volume of chloroform. Following concentration in vacuo the antibiotics contained within this concentrate were precipitated as solids (14.5 grams) on addition of heptane. The pH 8.0 aqueous layer was adjusted to pH 4.0 and twice extracted with one-fifth volume of chloroform. The chloroform extract was concentrated in vacuo and the antibiotics contained therein were precipitated as solids (45 grams) on addition of heptane.

An aliquot (4.0 g) of the solids from the pH 8.0 chloroform extract was chromatographed on a 92 × 2.54 cm column of pH 5.0 (50 g sodium dihydrogen phosphate monohydrate in 1 liter of water; 250 ml pH 5.0 buffer per liter silica gel $PF_{254}$) buffered silica gel $PF_{254}$ (E. Merck, Darmstadt, Germany) made up in chloroform. The solids were added in chloroform solution to the column and developed under 80 psi with chloroform:ethyl acetate (80:20% v/v). The column cuts were assayed by thin layer chromatography employing pH 5.0 silica gel plates developed with chloroform:ethyl acetate (50:50% v/v). Appropriate cuts were combined with evaporated in vacuo to afford amorphous Compound 42,405 (0.65 g) as a bright red solid. This material could not be induced to crystallize.

Latter cuts from the column afforded amorphous Compound 42,752 (0.16 g) as a bright red solid. This material could not be induced to crystallize.

Middle cuts from the column Compound 43,038 and Compound 43,139. Compound 42,405

Inspection of the elementary analysis and solubility data, ultraviolet absorption maxima and infrared bands led to direct comparisons with an authentic sample of rubradirin (*Streptomyces achromogenes* var. *rubradiris* NRRL 3061, U.S. Pat. No. 3,335,057). They were identical in all respects.

Compound 42,752

Elementary Analysis (sample dried overnight in vacuo at 55°–60° C.)

C — 61.11
H — 5.58
N — 3.81
O — 29.50 (by difference)

Solubilities

Soluble in chloroform, methylisobutyl ketone, dimethylsulfoxide and dimethylformamide; moderately soluble in methanol and ethanol; insoluble in hexane, heptane and water.

Ultraviolet Absorption Maxima $\lambda_{max}^{dioxane}$ 264, 324, 500 m$\mu$.
$E_{1cm}^{1\%}$ 345, 265, 20.

Characteristic Infrared Bands (KBr disc) in microns as shown in FIG. I.
3.00, 3.42, 5.82, 6.00, 6.14, 6.20, 6.37, 6.62, 7.58, 7.82, 8.92, 9.22, 9.75, 10.00, 10.75, 11.55 and 13.65.

EXAMPLE III

Those cuts from columns of Example II which were rich in Compound 43,038 and Compound 43,139 were combined and rechromatographed on pH 5.0 buffered silica gel $PF_{254}$. The column was developed with chloroform:ethyl acetate (70:30% v/v) and the development monitored by thin layer chromatography. The cuts rich in Compound 43,038 were pooled and subjected to preparative thin layer chromatography employing pH 5.0 silica gel plates developed with chloroform:ethyl acetate (50:50% v/v). The appropriate band was removed to afford Compound 43,038 as an amorphous red solid that could not be induced to crystallize. A similar procedure when applied to those column cuts rich in Compound 43,139 led to amorphous Compound 43,139 which could not be induced to crystallize.

Compound 43,038

Elementary Analysis
(sample dried overnight in vacuo at 55°–60° C.)
C — 59.13
H — 4.80
N — 4.61
O — 31.46 (by difference)

Solubilities

Soluble in chloroform, methylisobutyl ketone, dimethylsulfoxide and dimethylformamide; moderately soluble in methanol and ethanol; insoluble in hexane, heptane and water.

Ultraviolet Absorption Maxima $\lambda_{max}^{dioxane}$ 265$_{sh}$, 339$_{sh}$, 510 m$\mu$.
$E_{1cm}^{1\%}$ 267, 278, 15.

Figure 2:
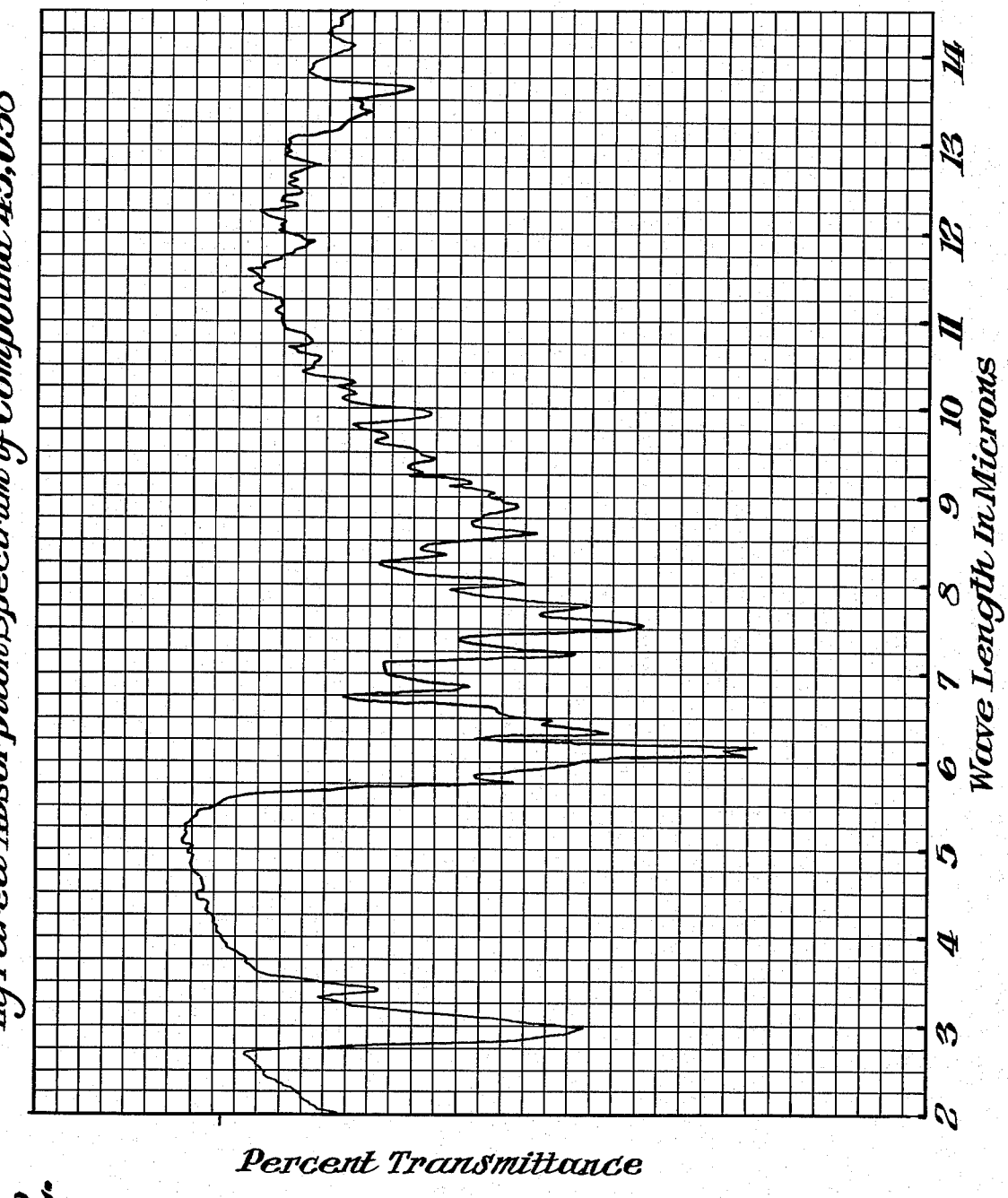

Characteristic Infrared Bands (KBr disc) in microns as shown in FIG. 2.
2.96, 3.40, 5.77, 5.98, 6.08, 6.19, 6.35, 6.50, 6.86, 7.25, 7.55, 7.78, 8.03, 8.35, 8.60, 8.90, 9.95 and 13.64,

Compound 43,139

Elementary Analysis (sample dried overnight in vacuo at 55–60° C.)
C — 60.39
H — 5.68
N — 4.07
O — 29.86 (by difference)

Solubilities

Soluble in chloroform, methylisobutyl ketone, dimethylsulfoxide and dimethylformamide; moderately soluble in methanol and ethanol; insoluble in hexane, heptane and water.

Ultraviolet Absorption Maxima $\lambda_{max}^{dioxane}$ 295$_{sh}$, 308$_{sh}$, 345$_{sh}$, 500 m$\mu$.
$E_{1cm}^{1\%}$ 222, 227, 214, 15,

Characteristic Infrared Bands (KBr disc) in microns as shown in FIg. 3.
2.97, 3.40, 5.77, 6.00, 6.08, 6.19, 6.50, 6.85, 7.25, 7.55, 8.04, 8.60, 8.95, 9.25, 9.92, 10.16, 11.55, 13.20 and 13.64

What is claimed is:

1. Antibiotic substance Compound 42,752 which is soluble in chloroform, methylisobutyl ketone, dimethylsulfoxide and dimethylformamide; moderately soluble in methanol and ethanol; and insoluble in hexane, heptane and water; has absorption maxima in dioxane in the ultraviolet light region of the spectrum at 264, 324 and 500 m$\mu$ with $E_{1cm}^{1\%}$ values of 345, 265 and 20, respectively; has the average composition by weight of 61.11% carbon, 5.58% hydrogen, 3.81% nitrogen and 29.50% oxygen (by difference); and when pelleted in KBr exhibits characteristic absorption in the infrared region at the following wavelengths in microns: 3.00, 3.42, 5.82, 6.00, 6.14, 6.20, 6.37, 6.62, 7.25, 7.58, 7.82, 8.92, 9.22, 9.75, 10.00, 10.75, 11.55 and 13.65.

2. Antibiotic substance Compound 43,038 which is soluble in chloroform, methylisobutyl ketone, dimethylsulfoxide and dimethylformamide; moderately soluble in methanol and ethanol; and insoluble in hexane, heptane and water; has absorption maxima in dioxane in the ultraviolet light region of the spectrum at 265, 339 and 510 m$\mu$ with $E_{1\ cm}^{1\%}$ values of 267, 278 and 15, respectively; has the average composition by weight of 59.13% carbon, 4.80% hydrogen, 4.61% nitrogen and 31.46% oxygen (by difference); and when pelleted in KBr exhibits characteristic absorption in the infrared region at the following wavelengths in microns: 2.96, 3.40, 5.77, 5.98, 6.08, 6.19, 6.35, 6.50, 6.86, 7.25, 7.55, 7.78, 8.03, 8.35, 8.60, 8.90, 9.95 and 13.64.

3. Antibiotic substance Compound 43,139 which is soluble in chloroform, methylisobutyl ketone, dimethylsulfoxide and dimethylformamide; moderately soluble in methanol and ethanol; and insoluble in hexane, heptane and water; has absorption maxima in dioxane in the ultraviolet light region at 295, 308, 345 and 500 m$\mu$ with $E_{1\ cm}^{1\%}$ values of 222, 227, 214 and 15, respectively; has the average composition by weight of 60.39% carbon, 5.68% hydrogen, 4.07% nitrogen and 29.86% oxygen (by difference); and when pelleted in KBr exhibits characteristic absorption in the infrared region at the following wavelengths in microns: 2.97, 3.40, 5.77, 6.00, 6.08, 6.19, 6.50, 6.85, 7.25, 7.55, 8.04, 8.60, 8.95, 9.25, 9.92, 10.16, 11.55, 13.20 and 13.64.

4. An antibiotic complex produced by cultivating *Micromonospora saitamica* sp. nov. Routien ATCC 31178 under submerged aerobic conditions in an aqueous nutrient medium containing an assimilable source of carbon and nitrogen until substantial antibiotic activity is obtained and separation said antibiotic complex therefrom.

* * * * *